United States Patent [19]

Terminiello et al.

[11] Patent Number: 4,790,979
[45] Date of Patent: Dec. 13, 1988

[54] TEST STRIP AND FIXTURE

[75] Inventors: Louis Terminiello, Sunrise; Jack L. Aronowitz, Delray Beach, both of Fla.

[73] Assignee: Technimed Corporation, Fort Lauderdale, Fla.

[21] Appl. No.: 901,603

[22] Filed: Aug. 29, 1986

[51] Int. Cl.$^4$ .................... G01N 31/22; A61B 17/34
[52] U.S. Cl. ........................ 422/56; 422/58; 436/170; 128/770; 128/771
[58] Field of Search ............... 422/56, 58; 128/770, 128/771; 436/169, 170

[56] References Cited

U.S. PATENT DOCUMENTS

| | | | |
|---|---|---|---|
| 3,061,523 | 10/1962 | Free | 436/169 X |
| 3,552,928 | 1/1971 | Fetter | 422/56 X |
| 3,607,093 | 9/1971 | Stone | 422/56 |
| 3,626,929 | 12/1971 | Sanz | 128/770 |
| 3,640,388 | 2/1972 | Ferrari | 128/771 X |
| 3,786,510 | 1/1974 | Hodges | 128/771 X |
| 4,042,335 | 8/1977 | Clement | 422/56 |
| 4,059,405 | 11/1977 | Sodickson et al. | 422/56 X |
| 4,094,647 | 6/1978 | Deutsch | 422/56 |
| 4,144,306 | 3/1979 | Figueras | 422/56 |
| 4,256,693 | 3/1981 | Kondo et al. | 422/57 X |
| 4,258,001 | 3/1981 | Pierce | 422/56 |
| 4,288,228 | 9/1981 | Oberhardt | 436/170 X |
| 4,337,222 | 6/1982 | Kitajima et al. | 422/56 |
| 4,340,565 | 7/1982 | Kitajima et al. | 422/56 |
| 4,366,241 | 12/1982 | Tom et al. | 422/56 X |
| 4,476,222 | 10/1984 | Ohtani et al. | 422/56 X |
| 4,478,944 | 10/1984 | Gross et al. | 436/170 X |
| 4,627,445 | 12/1986 | Garcia et al. | 128/329 R X |
| 4,637,403 | 1/1987 | Garcia et al. | 128/770 |
| 4,637,978 | 1/1987 | Dappen | 436/170 X |

Primary Examiner—Barry S. Richman
Assistant Examiner—Jill Johnston
Attorney, Agent, or Firm—John H. Faro

[57] ABSTRACT

A test strip is disclosed which provides for transport and separation of heterogenous fluid samples. This test strip can be used for analysis of whole blood by reflectance measurement. This test strip, which can be especially adapted for use in a disposable blood sampling fixture, comprises two functional components: (1) a wicking element for reception of the whole blood sample and transport of the sample to a dry chemistry reagent system, and (2) a porous membrane which has been impregnated with a dry chemistry reagent system specific for analysis of an analyte within the whole blood sample. A barrier layer is provided between the wicking layer and the porous membrane to preclude contact therebetween. In the preferred embodiments of this invention, an aperture is cut or formed in the barrier layer to allow for the flow of sample for the wick to the surface of the porous membrane. Such transport of sample does not, however, involve or contemplate physical between the wick and the membrane in the area of the aperture. This test strip is suitable for use in a disposable fixture designed for self collection and testing of the whole blood sample for one or more constituents (i.e. glucose).

7 Claims, 5 Drawing Sheets

TEST STRIP AND FIXTURE

BACKGROUND OF THE INVENTION

1. Field of the Invention

This invention is directed to an article of manufacture and to a method. More specifically, this invention concerns itself with a test strip which can be used in a disposable fixture designed for the collection of a whole blood sample on the test strip. The test strip itself has two functional component elements, one component of which (wicking element) is intended for the collection and transport of the sample from the sample application site, and the second component thereof (porous membrane) is intended for the separation of interfering constituents from that portion of the sample subjected to analysis. This test strip is unique in that neither functional component is in contiguous relationship with the other, nor is fluid transport effected through an intermediate layer. The indicator used in the analysis system is capable of measurement by reflectance technique (spectroscopy).

2. Description of the Prior Art

The analysis of biological fluids to confirm the levels of various biological products is an accepted clinical practice for the determination of proper functioning of the endocrine system. This practice is common in the diagnosis of diabetes and in the management of this disease. Blood sugar levels can generally fluctuate with the time of day and with the period since the individual's last consumption of food. Management of diabetes often, thus, requires the frequent sampling and analysis of the diabetic's blood for determination of its relative glucose level. The management of this disease by the diabetic will typically involve the sampling of his own blood, the self-analysis of the sample for its relative glucose content and the administration of insulin, or the ingestion of sugar, depending upon the indicated glucose level. A number of devices have recently appeared on the market to assist the diabetic in the self-testing of the blood sugar level. One such device, developed by Audiobionics (now Garid, Inc.)—described in U.S. Pat. No. 4,627,445, issued Dec. 9, 1986. to be introduced into the marketplace in the not too distant future—involves the use of a fixture containing a multi-layered element for the collection of the whole blood sample, the transport of the sample from the point of application on the element to a porous membrane, and the analysis of the blood sample for its glucose contents by the dry chemistry reagent system which is present within the porous membrane.

In the preferred embodiments of this disposable fixture, the whole blood sample is obtained by a pin prick of the diabetic's finger, the blood collected on a defined area of a wicking element, and transported from the point of application on the wicking element to the porous membrane containing the dry chemistry reagent system. The configuration of the blood collection/dry chemistry reagent system within the fixture is preferably designed to insure the uniform delivery of the whole blood to the membrane containing the dry chemistry reagent system. In the preferred embodiments of this device, the colored components of the blood are effectively isolated, or separated from the blood sample by the membrane or a separate element within the reaction zone prior to the interaction of the serum component of the sample with the dry chemistry reagent system. If glucose is present in the sample, the chemistry reagent system will interact therewith, thus, forming an indicator which can be measured by a reflectance spectrophotometer of the device for which the fixture is adapted.

The subject matter of this invention is directed to an improvement in this multi-layered element which can be used in the fixture of the device described in the previous referenced co-pending patent application.

Preliminary to description of the improvements of this invention, it will be helpful to place it in context by review of the relevant prior art.

The performance of glucose determinations on whole blood, utilizing multiple layered films, is the subject of numerous publications and issued patents. The following listing is representative of the publications in this area: *Dry Reagent Chemistries in Clinical Analysis*, Analytical Chemistry, Vol. 55, No. 4, pp. 498–514 (April, 1983); Curme, Henry G., et al., *Multilayer Film Elements for Clinical Analysis: General Concepts*, Clinical Chemistry, Vol. 24, No. 8, pp. 1335–1342 (August, 1978); Spayd, Richard W., et al., *Multilayer Film Elements for Clinical Analysis: Applications to Representative Chemical Determinations*, Clinical Chemistry, Vol. 24, No. 8, pp. 1343–1350 (August, 1978); Ohkubo, Akiyuki, et al., *Plasma Glucose Concentrations of Whole Blood, as Determined with a Multilayer-Film Analytical Element*, Clinical Chemistry, Vol. 27, No. 7, pp. 1287–1290 (July, 1981); Ohkubo, Akiyuki, et al., *Multilayer-Film Analysis for Urea Nitrogen in Blood, Serum, or Plasma*, Clinical Chemistry, Vol. 30, No. 7, pp. 1222–1225 (July, 1984); and, Rupchock, Patricia, et al., *Dry-Reagent Strips Used for Determination of Theophylline in Serum*, Clinical Chemistry, Vol. 31, No. 5, pp. 737–740 (May, 1985). The following listing is representative of the patent literature in this area: U.S. Pat. Nos. 3,061,523 (to Free); 3,552,925 (to Fetter); 3,607,093 (to Stone); 4,042,335 (to Clement); 4,059,405 (to Sodickson, et al); 4,144,306 (to Figueras); 4,258,001 (to Pierce); and, 4,366,241 (to Tom, et al).

The above publications contain a relatively complete description of the state of the art which are embodied within devices which are available from Eastman Kodak Company and from the Ames Division of Miles Laboratories. U.S. Pat. No. 3,061,523 (to Free), describes the basic chemistry reagent system which has become the standard for colorimetric determination of glucose in biological samples. The chemistry system described by Free is contemplated for use in conjunction with a "dip stick" test. In a typical configuration of the Free invention, a solid phase (i.e. sticks or test strips) is pre-treated with his novel chemistry formulation. The reagent treated portion of this solid phase can thereafter be contacted with a sample suspected of containing glucose. The intensity of color which is developed as a result of such contact is compared to a control or standard and a semi-quantitative determination of glucose level in the sample thereby computed.

In the specific embodiments of the Free device, the dry chemistry reagent system is prepared by first dissolving the reactive constituents in a gelatin base and thereafter impregnating strips of filter paper with this dry chemistry reagent system. This is achieved by simply immersing the filter paper in the gelatin base/reagent system for a sufficient interval to effect impregnation of the reagents into the filter paper. The filter paper treated in this fashion is thereafter dried. The gelatin component of the impregnating solution is reportedly essential to the uniformity of color development. Presumably, the presence of the gelatin controls or inhibits the migration of fluids within the filter paper, thereby minimizing chromatographic separation of reagents and/or sample.

A drop of blood (preferably whole blood) is then applied to the portion of the filter paper containing the dry chemistry reagent system; allowed to react with the reagents contained therein (for approximately 60 seconds) and, thereafter the blood (presumably the red cells) rinsed from the paper. The intensity of the color indicator which is developed as a result of the interaction of the glucose and the reagents within the paper, is thereafter observed or measured. The recommendation (if not a requirement), of the Free system, that the red cells be rinsed from the surface of the test strip, implies that their removal is desirable, if not essential, to observation/measurement of the colored indicator.

Where the technician performing this test is dealing with a patient sample that may contain infectious microorganisms or viruses, the requirement that the sample be rinsed of red blood cells unnecessarily exposes the technician to potential infection.

U.S. Pat. No. 3,552,925 (to Fetter), represents an improvement to the glucose test element described in the Free patent. Fetter discloses a method and device for effectively separating the whole blood sample into its serum components and into its erythrocyte components (red blood cells and other color forming constituents). Fetter achieves this separation by treatment of a defined area of his sample collection device on his test element with certain water soluble salts. The contact of the whole blood sample with these salts in the test element results in the localized reaction of the erythrocytes (and the other colored components of the whole blood) with these salts with the resultant separation of the serum component therefrom. The serum fraction is, thus, free to migrate or diffuse into the test element. The migration and/or diffusion of the serum component is generally via capillary action or some other passive transport mechanism. The manner in which the sample is applied and the nature of the test medium, effectively transports and distributes the serum to another defined chemically reactive area of the test element containing test reagents. The test reagents of the test element are specific for one or more analytes of interest in the serum fraction (i.e. glucose, galactose, urea, uric acid, phenylalinine and/or various enzymes).

The various configurations of the Fetter test element contemplate a single laminae (FIGS. 1 and 8), having discrete areas of chemical treatments; or a multi-layered structure, wherein a single chemical treatment is confined to each of the layers of the laminate (FIGS. 3 through 7).

Fetter also indicates that the same matrix can be used to retain both the separating reagent and the reagent specific for the analyte of interest. In this latter embodiment of his invention, the whole blood sample would be applied to one side of the strip held in the horizontal position. After adequate penetration of the sample into the matrix containing both the separating and test reagents, the test strip would be inverted and color development observed (if any) on the site opposite the site of application of the whole blood sample. Fetter is not apparently concerned with potential interference of the colored blood components with the development and/or observation of the indicator species. It is, however, apparent that at low concentrations of analyte, the highly colored blood components would interfere and/or mask the presence of the indicator from visual observation/detection.

U.S. Pat. No. 3,607,093 (to Stone), describes the use of a filtration membrane as an analytical element for glucose analysis of whole blood. The membrane is pretreated with a chemical reagent system for glucose detection, and dried whole blood is applied to a dense surface of the membrane. The cellular components remain on top of the membrane, while the serum fraction is absorbed and reacts with the reagent system. The Stone configuration, as contemplated, is not readily adapted to instrument monitoring for the reasons given in the discussions of the shortcomings of the system described in the Free and Fetter patents.

U.S. Pat. No. 4,042,335 (to Clement), describes a multi-layered analytical element suitable for performing chemical analysis of whole blood samples. The Clement configurations all contemplate the application of test samples either directly, or from a spreading layer, to a reagent layer. The reagent layer contains a complement of chemicals for reaction with a specific analyte suspected of being present in the test sample. If the analyte is present, a "detectable species" is formed or released from the reagent layer and diffuses into what is termed a "registration layer"—that is, a layer whose *sole* function is to provide a medium or repository from which the detectable species can be observed or measured. In order to avoid interference (masking) in the observation or measurement of the detectable species, the registration layer is both devoid of the test sample and reagents used in the generation of the diffusable species. In the preferred embodiments of the Clement test element, an optical screen ("radiation blocking layer") is also provided between the reagent layer and the registration layer. This optical screen effectively optically isolates the detectable species from other constituents which could interfere in its detection and/or measurement.

As is evident from the foregoing description, Clement attempts to segregate the individual functions of his analytical element into discrete layers. This technique, although potentially attractive to a manufacturer in possession of technology for fabrication of multi-layered elements, is by its very nature unduly complex and potentially prone to mechanical instability of the composites. More specifically, where this test element is to be used by an individual in a self-test environment, the composite must necessarily be supported on an additional element to lend physical integrity to the multi-layered element and thereby prevent its unintended flexing and potential separation of the various layers contained therein.

U.S. Pat. No. 4,059,405 (to Sodickson, et al), describes a method and apparatus for glucose analysis of whole blood samples. In the Sodickson system (as described in Example I d.), a reaction site is initially prepared by preforming wells in a polyox resin treated filter paper. A reaction site is physically defined in this treated paper by impressing thereon a confining ring approximately one centimeter in diameter. A glucose reagent is then applied to the reaction site defined by this ring and the reaction site dried. An ultrafiltration membrane is placed over the well and a sheet of paper containing a dried blood spot placed in contiguous relationship with the ultrafiltration membrane. The dried blood spot is then reconstituted by the addition of saline. The apparatus used in the Sodickson system (i.e. press) confines the reconstituted blood sample in the reaction well for a brief period. During this incubation period, soluble components of the whole blood sample are redissolved in the saline and pass through the ultrafiltration membrane where they come in contact with the glucose test reagents in the polyox treated paper. The cellular components of the blood are retained on the ultrafiltration membrane and thereby prevented from interference and measurement of the glucose manifesting indicator.

The system described by Sodickson, as contemplated in his Example I d., is cumbersome (requiring reconstitution of the blood sample and relatively complex equipment to effect separation of cellular components from the whole blood sample) and does not readily lend itself to self-testing.

U.S. Pat. No. 4,144,306 (to Figueras), describes a multi-layered analytical element analogous to that of the Clement patent (previously discussed). The Figueras chemistry differs from Clement in that the interaction of an analyte and non-diffusable reagents in the reagent layer, results in the release of a "preformed detectable species" which can migrate from the reagent layer into a registration layer. This performed detectable species is then observed or measured in the registration layer. Figueras contemplates (as described in Example VI) the adaptation of his system to glucose analysis of whole blood. The separation of colored and cellular components of the whole blood would be achieved by Figueras in essentially the same fashion as in the Clement patent. The introduction of the whole blood sample into the reagent layer of the Figueras element results in the release of a diffusable preformed photographic dye, which is then free to migrate into the registration layer. Figueras requires the presence of the same type of optical screen (radiation blocking layer) between the reagent layer and the registration layer to avoid masking or interference in detection of the dye from the nondiffusable color components (i.e. sample and reagents) in the reagent layer. The limitations and disadvantages noted in the discussion of the Clement patent are also applicable to the multi-layered analytical element of Figueras. Figueras, however, introduces an initial complexity; namely, the effective immobilization of the reagents within the reagent layer and the preservation of the preformed indicator prior to its release by the analyte of interest. Because of the requirements of maintenance of fluid contact between the various elements of the Figueras composite, its mechanical properties are critical. Accordingly, the multi-layered element of Figueras, as previously noted for Clement, will require a supporting (transparent) layer to lend physical integrity to this device.

U.S. Pat. No. 4,258,001 (to Pierce et al), describes a multi-layered analytical element (of the type described in both Clement and Figueras—previously discussed) incorporating a unique spreading layer. The spreading layer of the Pierce patent is described as an essentially "non-fibrous" material. In one of the preferred embodiments described by Pierce (FIG. III), the spreading layer can contain "interactive compositions" (test reagents) for reaction with analytes in a test sample. Pierce also contemplates the use of her device in the analysis of whole blood, blood serum and urine. Whole blood can be applied directly to the Pierce element. The presence of red blood cells will not reportedly interfere with spectrophotometric analysis if carried out by reflectance measurements, provided a radiation screen (blocking layer) is used to screen out interference from the red cells (column 26, line 49-61).

As is evident from this patent, the Pierce device is designed to "take up" the whole blood sample. Thus, both cellular and non-cellular components of the whole blood are imbibed by the spreading layer. The spreading layer of Pierce is, thus, not intended nor contemplated as a means for separation of the cellular fraction of the blood from the serum fraction. Where enzyme based diagnostic clinical assays are incorporated into the spreading layer (as in the case of glucose analysis), the potential for inhibition of these enzymes by the erythrocytes can potentially mask low concentrations of glucose and, thus, distort an otherwise clinically significant result.

The transport and spreading of biological samples is of concern, not only in clinical chemistry system of the type described in the above patents, but also in immunoassays of the same biological fluids. The following U.S. Patents are representative of the literature in this area: U.S. Pat. No. 4,094,647 (to Deutsch); and U.S. Pat. No. 4,366,214 (to Tom et al).

U.S. Pat. No. 4,094,647 (to Deutsch), describes a linear wick having defined areas for placement of reagents and sample. The end of the wick is placed in a vertical position as a developer fluid and the fluid drawn up the wick by capillary action. As the fluid is drawn into the wick, it transports the reagents and sample, from their respective locations, into contact with one another. One or more of these reagents can be immobilized on the wick; thus, the developer fluid is used to transport reagent and sample to the immobilized reagent and any unreacted or mobile materials from the immobilized reagent. The site having the immobilized reagent can then be viewed or measured for the presence of analyte.

U.S. Pat. No. 4,366,241 (to Tom et al) describes a device for the non-chromatographic immunoassay of biological fluids. In the Tom assay device configuration, a test element, having a relatively small test zone, is treated with an immobilized binding material (termed "mip" or "member of an immunological binding pair"). The test zone of this device is the exclusive entry port for the biological sample and is designed for receipt of the biological sample either by direct application or immersion in the test fluid. The analyte (if any) contained in the biological sample is selectively (immunochemically) bound in the test zone to the immobilized binding material which is specific for this analyte. The residual components of the sample including the fluid component thereof, are drawn from the test zone to a second element which is in fluid contact (contiguous relationship) with the test zone. The second element's function is to pump or draw the biological sample through the test zone into the test element. Those constituents of the sample which are not bound in the test zone are, thus, drawn into the test element and away from the test zone.

In the immunological test element of the type described by Tom, the pretreatment of the test zone effectively confines the analyte and the test reagents (i.e. labelled indicator) to the analysis site, thereby effectively eliminating the problems of reagent and sample migration which are common in the solid phase systems designed for clinical chemistry analysis. These immunoassay systems of Tom are not, however, without their disadvantages, the most common being the nonspecific binding of interfering substances in the reaction zone and the difficulties which are sometimes inherent in the detection of low levels of analyte.

As is evident from the foregoing discussion of the references suitable for whole blood analysis, each type of element generally requires a plurality of lamina in its preferred configuration. Where a single layer (component) test device is suggested, none of the references, with one exception (U.S. Pat. No. 3,607,093-to Stone), either acknowledge or appreciate the potential chemical and optical interference of the erythrocyte population (and other colored components of the blood), on the analytical protocol or in the detection of the reaction product which is indicative of the presence of the analyte (namely, the glucose). Where immobilization techniques (as described in Fetter, Deutsch and Tom) are employed, the specificity of the binding reaction can, under certain conditions, be indiscriminate. In the case of Fetter, the attempt at scavenging of erythrocytes and other colored components from the sample with certain salts that have been imbibed within the test medium, is not without its limitations. In the single layered element of Fetter, the serum fraction is readily radially separated from the colored component of the blood and thereby results in the distribution of the analyte over a relatively large area. If the analyte is present in low concentrations, it can easily escape detection. Thus, some amplification mechanism may be required for visualization of a low level of analyte (the use of an enzyme in conjunction with a chromogenic substrate).

The immunochemical device and techniques of the type described by Deutsch and Tom are not readily compatible with whole blood analysis. It is possible to wash the test cell for removal of the cellular debris (as is suggested in the Free patent), however, the effect of such additional step upon the immunochemical binding process is not known and exposes the clinician or the person performing the test to potential infection by those components of the blood which are removed from the test element.

In summary, it should now be apparent that the prior art lacks a simple yet accurate device for glucose analysis of whole blood. Where such devices have been proposed, they are complex, do not readily lend themselves to self-testing without the provision of a fixture or additional support mechanism, and generally lack the sensitivity to permit differentiation of different levels of analyte over a broad clinical range of concentration. Moreover, all such devices discussed above (with the exception of the Stone patent) would appear to have one common failing; namely, their inability to effect optical (and in certain instances, chemical) isolation of erythrocyte and other colored components of the whole blood from the observation/measurement site without the physical removal of the erythrocytes from the test element; or, the provision of some optical screen (blocking layer) between the colored components of the sample and the indicator compound which is generated as a result of the clinical assay.

OBJECTS OF THE INVENTION

It is the object of this invention to remedy the above as well as related deficiencies in the prior art.

More specifically, it is the principle object of this invention to provide a test strip suitable for adaptation to a self-test device/fixture which effectively isolates the sample collection function from the component of the strip containing a dry chemistry reagent system.

It is another object of this invention to provide a test strip for heterogenous fluid samples which includes a laminate of a wicking element and a porous membrane containing a dry chemistry reagent system.

It is yet another object of this invention to provide a test fixture which incorporates a whole blood test strip, said fixture having a means for drawing a blood sample and transferring the sample to the test strip.

It is still yet another object of this invention to provide a test strip which effects rapid transport and distribution of the sample from the application site to the analysis and rapid self equilibration of sample with the analysis site.

It is a further object of this invention to provide a method for the collection and analysis of a whole blood sample through the use of a self-test device which utilizes a disposable test fixture having a whole blood test strip.

SUMMARY OF THE INVENTION

The above and related objects are achieved by providing a composite test strip having two functional layers: (1) a wicking element for reception of a heterogenous fluid sample and transport of the sample to a dry chemistry reagent system and, (2) a porous membrane which has been impregnated with a dry chemistry reagent system specific for analysis of an analyte within the heterogenous sample. The term "heterogenous" as used throughout this disclosure is intended as inclusive of a fluid having suspended and/or dissolved matter which is not involved in the analysis of the sample; and which can either interfere with reaction of the dry chemistry reagents with the analyte of interest or mask the results of such reaction. It is one of the primary objects of this test device to separate such suspended or dissolved matter within the test strip (preliminary to interaction of the analyte and reagents) and physically isolate such suspended and/or dissolved matter from masking the results (indicator) of such interactions.

A barrier layer is provided between the wicking layer and porous membrane to preclude both physical and fluid contact therebetween. In the preferred embodiments of this invention, an aperture of predetermined size is cut or formed in the barrier layer to allow the flow of sample from the wick to the surface of the porous membrane. This aperture defines a well into which the sample can flow from the wicking element. Generally, the size and dimension of this aperture will approximate the size and dimension of area of the observation field. Such transport of sample does not, however, involve or contemplate physical contact between the surface of the wick and the surface of the membrane in the area of the aperture. In the preferred embodiments of this invention, the porous membrane has been impregnated with a dry chemistry reagent system that is specific for one or more constituents which are native to whole blood.

This test strip can be readily adapted to a fixture for self-testing. The relationship between the test strip and the fixture provide an effective disposable element for use in conjunction with a self-test monitor. This fixture typically will include a lance, or its equivalent, supported on a movable leaf spring. In the preferred embodiments of this invention, the wick of the test strip is positioned within the fixture in proximate relationship to the lance. In an alternative embodiment of this invention, the wick portion of the test strip can be in contiguous relationship with the lance and the lance penetrate through the wick in the process of inflicting a puncture wound to the user's finger.

As presently contemplated, the disposable fixture will be inserted into a self-test device equipped with a spring activated impeller and a photo optical system sensitive to the development of an indicator compound within the test strip. This indicator compound will be produced as a result of a chemical reaction of a constituent of the fluid sample (i.e. glucose) and the dry chemistry reagent system within the porous membrane of the test strip.

In the operation of this device, the user will arm or cock the impeller, place his finger on or in close proximity to the lance of the disposable fixture and activate (trigger) the impeller. The impeller will impact the spring supporting the lance and drive the lance into the user's finger, thereby causing a puncture wound sufficient to draw blood. Once the force of the impeller has been released and transferred through the leaf spring to the lance, the impeller is withdrawn into the self-test device. The recoil action of the leaf spring withdraws the lance back into the test fixture. The user, however, maintains the puncture wound in contact with the fixture at or near the aperture through which the wick of the test strip is exposed. A sample of whole blood (as little as 10 microliters of blood) is thusly applied to the wick and taken up, to the extent necessary, to effect its transport from the application site on the test strip to that portion of the test strip in which the sample is accessible to the membrane containing the dry chemistry reagent system.

In the preferred embodiments of this invention, the disposable test fixture is maintained in an analytical relationship with the reusable self-test device. As noted above, the transport of the whole blood sample by the wick of the test strip is, thus, calculated to convey the whole blood sample from the point of application to the wick to the area of the test strip in which the wick is accessible to the porous membrane. After the sample proceeds to flow into this area of the test strip and onto the top surface of the membrane, it initiates a colorimetric reaction with the membrane and triggers a timer of the reusable self-test device. After the elapse of a prescribed interval (generally 60 seconds), a photometric measurement of the indicator is made from the underside of the porous membrane. In the most preferred embodiments of this invention, the dry chemistry reagent system of the porous membrane are specific for reaction with and the manifestation of glucose in the blood sample.

DESCRIPTION OF THE INVENTION INCLUDING PREFERRED EMBODIMENTS

Figure 1:
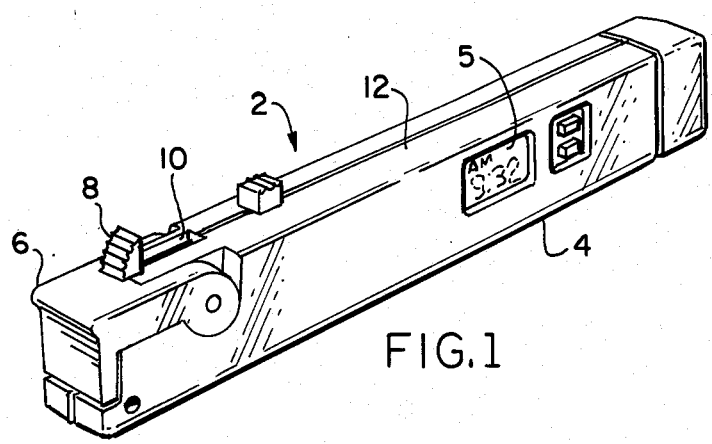
FIG. 1 is a perspective view of a self-diagnostic monitor for sampling and measurement of blood glucose levels.

The description which follows is in reference to the various figures attached to and made part of this application. Where an element is common to more than one figure, it is assigned a common reference numeral.

Figure 2A:
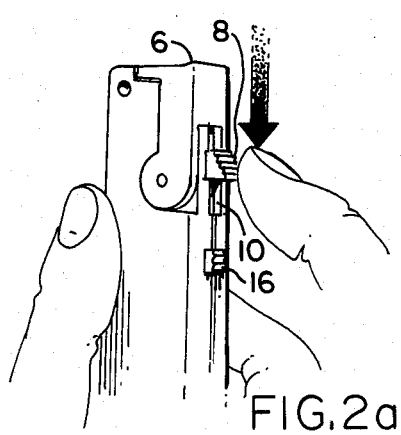
FIGS. 2A-2F are a series of drawings illustrating the operation of the self-diagnostic monitor of FIG. 1.
Figure 2B:
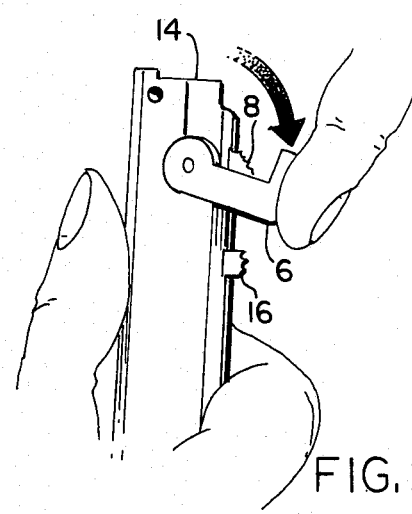
Figure 2C:
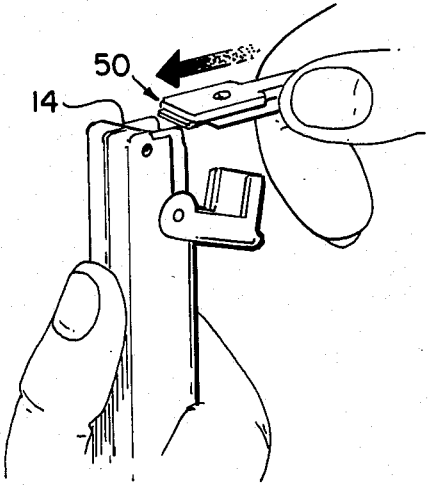
Figure 2D:
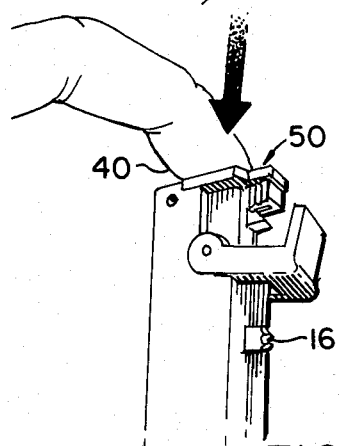
Figure 2E:
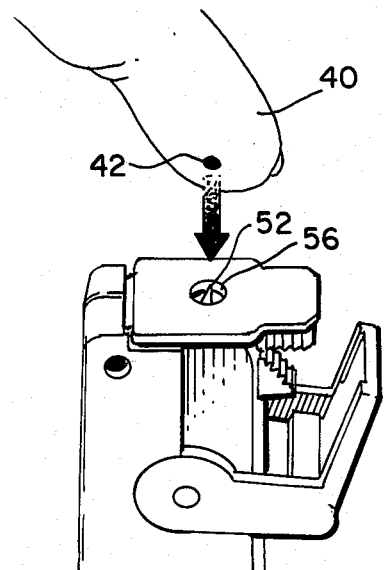
Figure 2F:
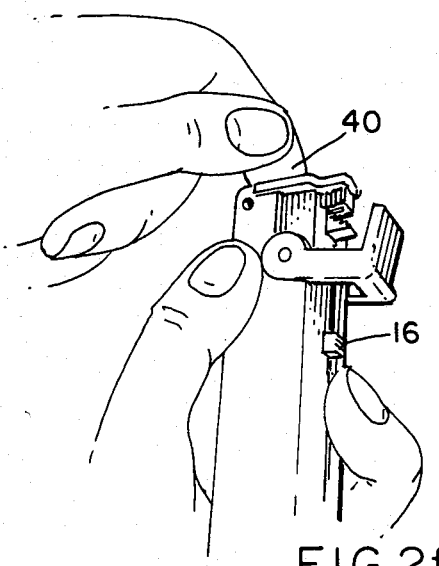

FIG. 1 illustrates a perspective view of the self-diagnostic monitor (2) which can be used in conjunction with the test strip and dedicated reagent system that are the subjects of this patent application. In brief, this self-test diagnostic monitor includes a housing (4), having disposed on one end, a hinged or pivoting cover (6) which can be opened to expose a photo optical read station and the mechanism which is adapted to engage the dedicated reagent system for this monitor. The cover (6) is opened by simply sliding a release button (8) from one end of a slot (10) on the top surface (12) of the monitor to the other end of the slot. The movement of the button in this fashion, as illustrated in FIG. 2A, releases the cover thereby allowing it to be opened (FIG. 2B). This movement of the release button also performs the additional function of arming an impeller mechanism within the monitor. This arming operation simply involves the compression of an interval spring-like energy storage device (not shown). As illustrated in FIG. 2C, once the cover has been opened, the dedicated reagent system (50) can be inserted into the opened end (14) of the monitor. The dedicated reagent system (50) is more fully illustrated, in an exploded view in FIG. 3. This dedicated reagent system comprises a lance (52) attached to a leaf spring mechanism (54). The insertion of the dedicated reagent system into the monitor, as illustrated in FIG. 2C, places the leaf spring in essentially direct opposing relationship to the impeller (not shown) within the monitor. The user of this device then places his index finger of his left hand (40) over the aperture (56) of the dedicated reagent system. The impeller is activated by depressing a trigger button (16) with his other hand, as shown in FIG. 2D. This trigger releases the impeller spring, thereby causing the impeller to impact the leaf spring (54) of the dedicated reagent system, as illustrated in FIGS. 2E and 2F. The result of such impact is to drive the lance into the user's finger, thereby effecting a puncture wound sufficient to draw blood. The user maintains his finger with the puncture wound in proximity (contact) with the aperture of the dedicated reagent system. Blood from the wound is, thus, permitted to contact the wick of the test strip within the dedicated reagent system.

Sufficient blood is transferred (at least 10 microliters) to the wick to effect transfer of the sample to that portion of the test strip accessible to the dry chemistry reagents specific for analysis of the analyte of interest (i.e. glucose).

The transport of fluid within the test strip (60) and/or the activation of the trigger mechanism (14) can also begin the running timer within the monitor. After a finite interval, the photo optical system within the monitor (not shown) will record the level of color indicator that is generated as a result of interaction of the blood sample and the dry chemistry reagent system. The indicator level will be indicative of the amount of analyte in the sample. In a monitor of this type, a transducer within the monitor converts the sensed reflectance measurement to a voltage indicative of the level of indicator. A microprocessor within the monitor compares this voltage to a stored value and reports the perceived level of glucose in the blood sample. This value (amount of analyte, i.e. glucose) can be displayed on the light emitting diode (LED) display (5) of the monitor. The results of this test can also be stored within a microprocessor within the monitor for later comparison or reporting.

Figure 3:
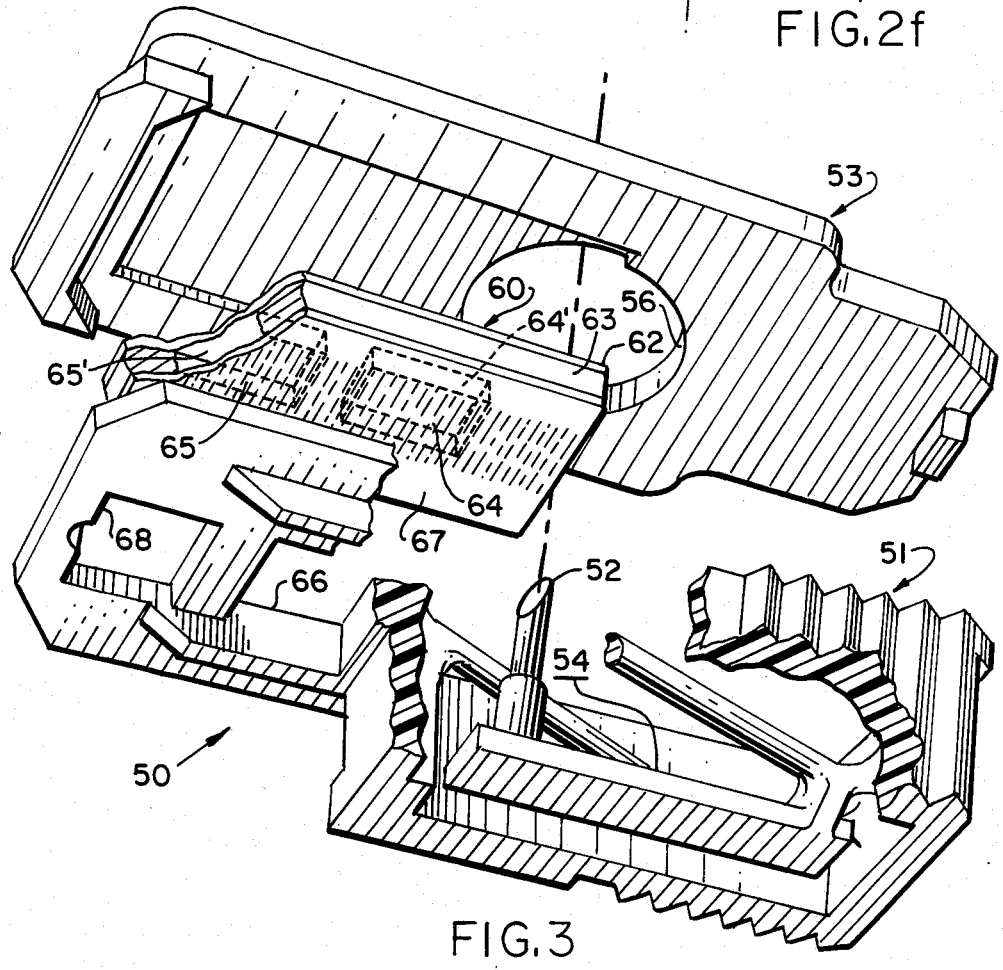
FIG. 3 is an exploded view of the disposable fixture adapted for use with the monitor of FIG. 1.

The dedicated reagent system used in this monitor is more fully illustrated in detail in the exploded view provided in FIG. 3. This device comprises a body which includes a frame (51) and a base plate (53). These two structural components support the mechanism (52, 54) for obtaining the whole blood sample and the test strip (60) containing the dry chemistry reagent used in analysis of the sample. The mechanism used in obtaining the sample is a simple leaf (54) spring/lancet (52) arrangement. Upon insertion of this dedicated reagent system into the monitor, as illustrated in FIG. 2C, the leaf spring is positioned relative to an impeller mechanism. Upon triggering the impeller mechanism, it impacts the leaf spring. This impact displaces the lancet, from its resting position, through the aperture (56) in the base plate. In the contemplated use of this self-test device, the user will maintain his finger (40) positioned against the aperture (56) thereby resulting in a puncture wound (42). After inflicting the puncture wound, the leaf spring withdraws the lancet back into the fixture. The puncture wound is of sufficient depth to draw blood from the user's finger. The user simply maintains his finger (4) in contact with the aperture (56). Blood from the user's finger (not shown) is drawn into the wicking layer (62) of the test strip (60). The wicking layer (62) transports the whole blood sample from the aperture to an analytical test site (64) which corresponds to an optical window (66) in the fixture body (51). This optical window (66) is aligned with a spectrophotometer contained in the monitor body. After a suitable interval has elapsed between the time of contact of the sample and the dry chemistry reagent system within the porous membrane (67) of the test strip, the spectrophotometer will measure, by reflectance, the relative concentration indicator in the porous membrane (67). A second site (65) is provided in the test strip which is essentially devoid of reagents. The transport of sample by the wick to the second site is also monitored by the spectrophotometer through a second window (68) in the fixture body. The detection of fluid by the spectrophotometer at this second site simply confirms the saturation of the test site (64) containing the reagents.

The monitor can be programmed to take but a single measurement (end point determination) or take a series of measurements at different time intervals (kinetic measurement). In both instances, the data processing logic of the microprocessor within the monitor will correlate the reading (color intensity) with some standard stored within its data base. The monitor will, thus, be able to display a reading on the LED display (5) which is indicative of the amount of analyte (i.e. glucose) within the blood sample.

The test strip utilized within the dedicated reagent system is believed to be of a unique configuration. This test strip, more fully illustrated in cross section in FIG. 3, comprises a wicking layer (62), a barrier layer (63), and a porous membrane (67) which has been pre-impregnated with a dry chemistry reagent system at an analytical test site (64). The blood sample, as noted previously, simply contacts the wicking element (62) of the test strip and is drawn by capillary action or some other transport mechanism along the surface of the wick. The barrier layer of the test strip effectively confines the fluid sample to the wicking layer. As illustrated in FIG. 3, an aperture (64') is provided in the barrier layer which defines to an analytical test site. This test site also corresponds to a window (64) in the body of the fixture (51). A similar aperture (65') is provided in the barrier layer at the second site (65). It is particularly noteworthy that the porous membrane and wicking layer are not in physical contact at any point within the test strip. Even where an aperture (64' or 65') is provided in the barrier layer, the two functional components of the strip remain remote from one another.

In order to facilitate flow of sample from the wick to the surface of the porous membrane, the wicking layer is modified in the region of the apertures (64', 65'). This modification involves a series of cuts or channels (not shown) in the surface of the wick contiguous with the barrier layer, in the area defined by the apertures in the barrier layer.

The physical characteristics (i.e. density) of the porous membrane (67) effectively preclude substantial penetration of particulates, notably, cellular components, from absorption into the porous membrane. In the preferred embodiments of the porous membrane used in the test strip, the surface of the membrane contiguous with the barrier layer is more dense (less porous) than the opposing surface of the membrane. Membranes which have proven suitable for use in this device are commercially available (i.e. Millipore MF filters, 0.10 to 0.45 $\mu$m; Metrical Membrane Filter, type GN-6, TMC-200 or TMC-450). The other physical characteristics and hydrophibic properties of the porous membrane favor and assist the absorption of the noncellular fluid constituents of the sample; and, thereby uniformly distribute it with in and among the dry chemical reagents which have been previously imbibed into the porous membrane. The reaction of the serum fraction of the whole blood sample with these reagents results in the development of an indicator species which is indicative of an analyte for which the dry chemical reagent system is specific. The indicator can be a chromophore or a fluorophore. Accordingly, its presence can be detected by reflectance spectrophotometry or front surface fluorometry. In the embodiment of the monitor illustrated in the drawings, reflectance spectrophotometry is the preferred method for detection of the indicator species. The presence of the indicator species is relatively easy to detect, since the other color components of the sample have been effectively excluded from substantial penetration into the porous membrane, thereby avoiding masking of the indicator and/or interference with its development.

The presence of the barrier layer intermediate between the wicking layer and the porous membrane unexpectedly enhances the dynamic range of the test strip. This is of particular importance where these test strips are adapted for use in a portable monitor; and, the power supply and monitor design only permit a very limited range (i.e. of voltage) in which to differentiate the various levels of analyte within the fluid sample.

In the portable monitor developed by Garid, Inc., (and referenced in the section of this application entitled "Description of the Prior Art"), the instrument is inherently limited in effecting differentiation in the incremental levels over a dynamic range of approximately four volts. Where such instrument is intended to provide clinically significant information over a relatively narrow range (i.e. 25 mg/dl to 100 mg/dl), the ability to differentiate levels of analyte over this dynamic range is relatively simple. Where, however, the clinically significant levels of analyte span a range of, for example, 25 mg/dl to 600 mg/dl, the instrument must detect such incremental differences and differentiate between them within a relatively narrow and limited voltage range of operation. In this latter situation, a portable monitor may not provide effective separation of the incremental differences in such analyte levels to permit their differentiation from one another.

Figure 4A:
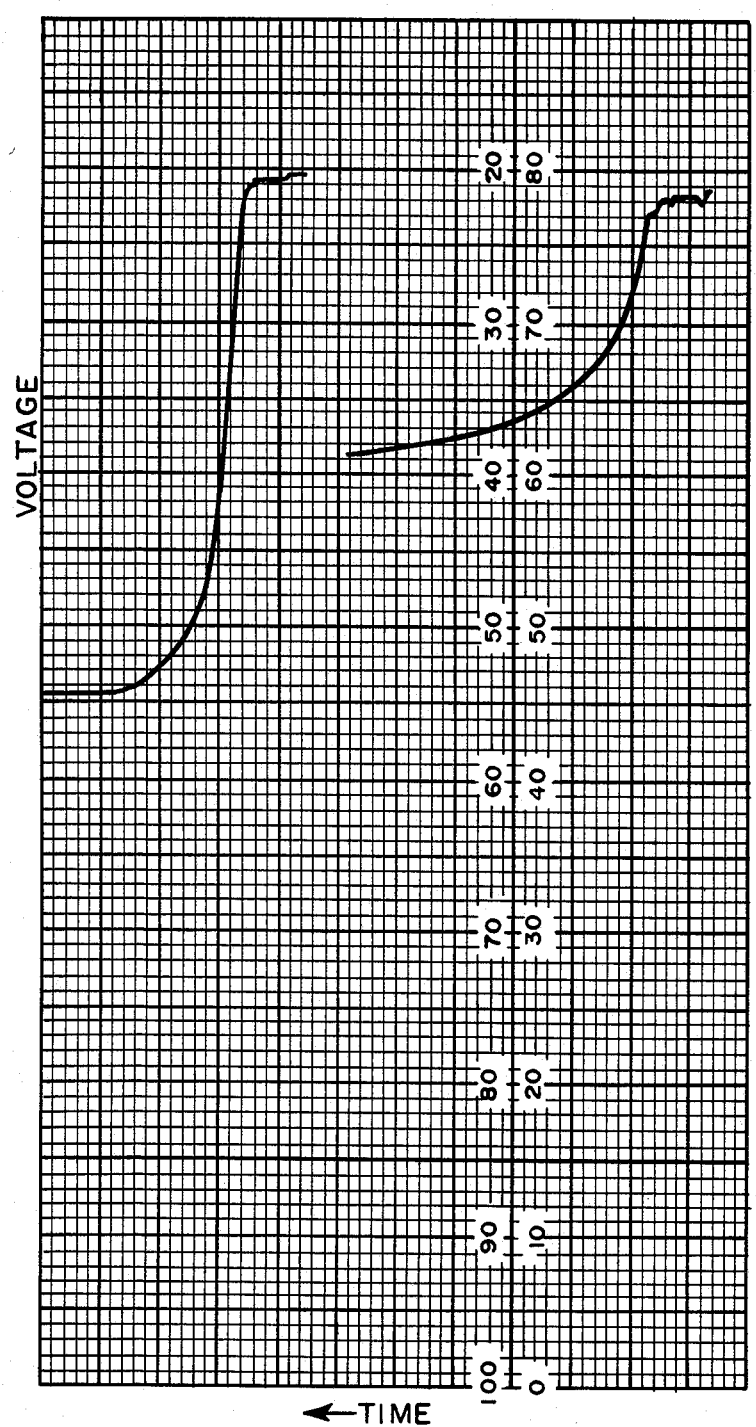
FIG. 4 is a graphical comparison of the effect of the barrier layer upon the dynamic range of performance of the reagent test strip of this invention.
Figure 4B:
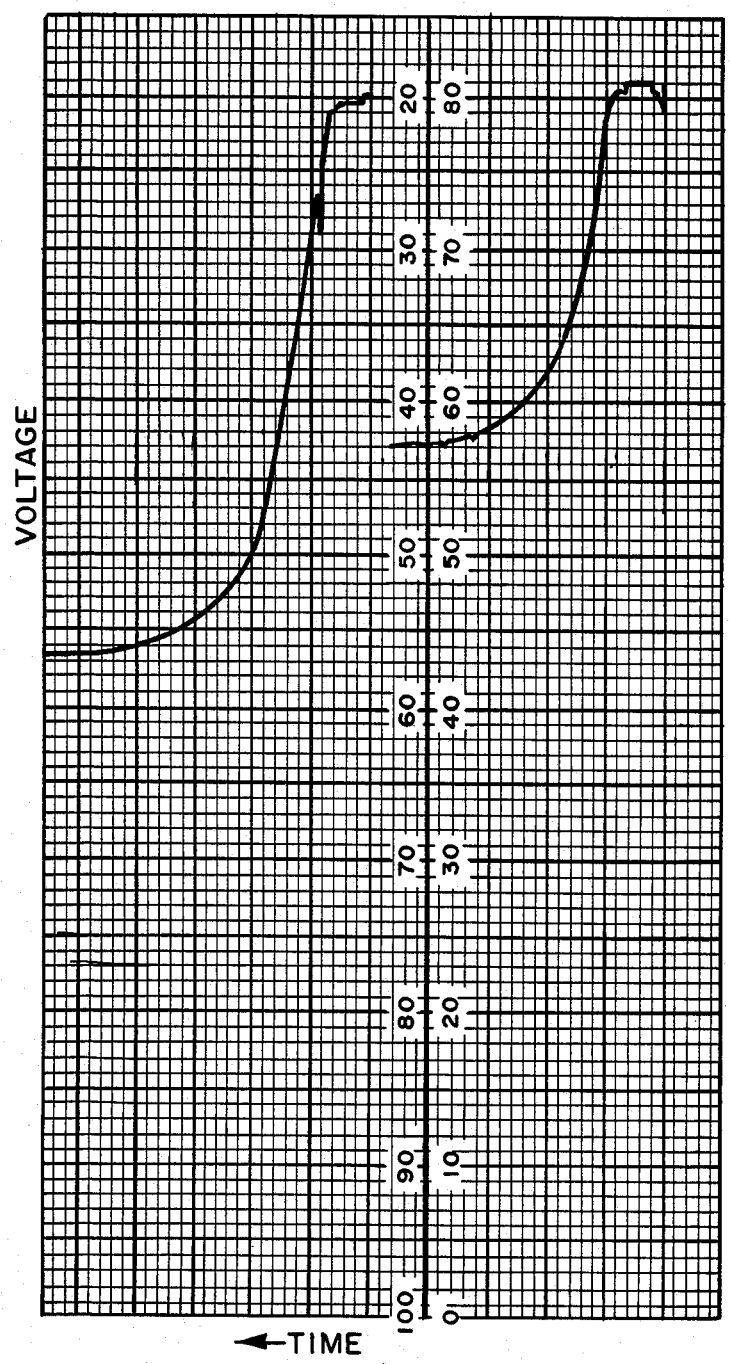
Figure 4C:
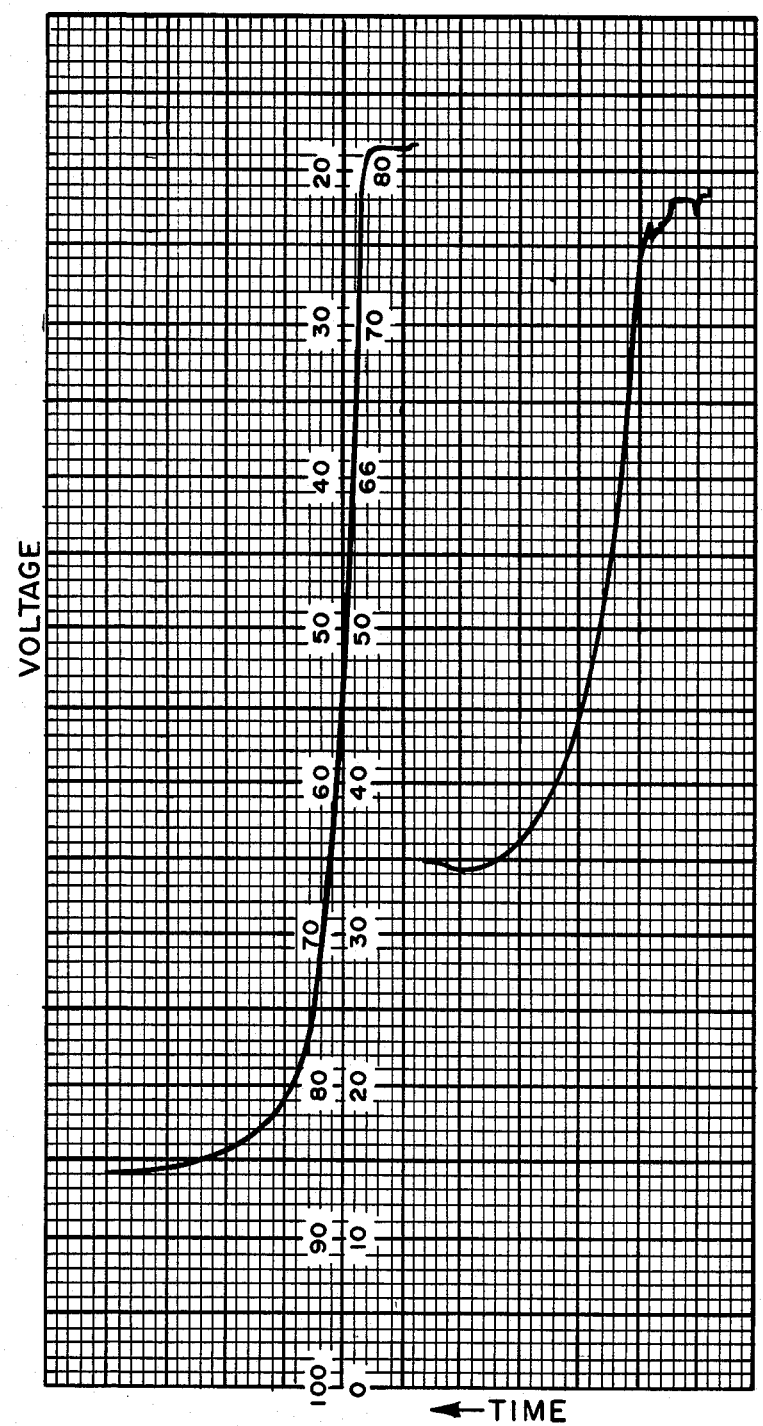

FIG. 4 provides a series of three (3) comparisons for a standard glucose solution at three (3) different levels of concentration. In each graphical illustration, the curve on the right represents the performance of a test strip with a barrier layer and the curve on the left represents the performance of a comparable test strip without a barrier layer. The standard glucose solution in FIG. 4A contains 25 mg/dl; in FIG. 4B, 90 mg/dl; and in FIG. 4C, 282 mg/dl. The dynamic performance range of the portable monitor is four (4) volts. As is evident, the voltage differential is 1.66 volts for the curve on the left of each of the graphs in FIGS. 4A and C, with the voltage of FIG. 3C for 282 mg/dl being at 3.37. If, however, the clinical significant range of analyte (in this case, glucose) is from 25-600 mg/dl, the monitor will not possess the ability to detect incremental changes in glucose level significantly above 300 mg/dl. In addition, the voltage differential of 1.66 volts (from 25 mg/dl to 282 mg/dl) may not be sufficient to detect incremental differences in analyte levels within this dynamic range.

By way of contrast, the curve on the right of each of FIGS. 4A, B and C, graphically represents better differentiation of the incremental difference in the level of glucose from each sample, and in addition, insures the extension of the dynamic range of the monitor to the higher clinical significant levels of analyte (above 300 mg/dl).

As is evident from the foregoing discussion, the configuration of the test strip provides a unique and convenient package for collection, transport, separation and analysis of heterogenous fluid samples, such as whole blood. This is achieved without interference from the highly colored constituents which are present in whole blood and without the necessity for separation of these constituents from the serum fraction prior to such analysis. This system also is significant in its design and operation in that the sample is confined within a matrix, thereby preventing exposure of another individual to potential infection or disease.

As should be readily apparent from the foregoing description, the test strips of this invention can also be used in the analysis of industrial fluid samples; in doctor's office analytical systems; and, in a quality control environment. The dry chemistry incorporated wtihin the porous membrane of this test strip can also be readily adapted for the performance of immunoassay and hybridization assays. The foregoing description is intended as illustrative of some of the preferred embodiments of a dedicated reagent system of this invention. It is not, however, intended as delineating its scope which is set forth in the claims which follow.

What is claimed is:

1. A self-contained analytical element for conducting an analysis of a heterogeneous fluid sample suspected of containing an analyte of interest comprising:

a test strip consisting essentially of two functional components, each of said functional components being maintained in spaced apart relationship and out of fluid contact with one another by a fluid impermeable barrier layer;

a first functional component of said test strip comprising an essentially planar wicking element for reception of the heterogeneous fluid sample and transport of the heterogeneous sample to a sample receptive surface of a porous membrane which has been impregnated with a dry chemistry reagent system;

a second functional component comprising an essentially planar porous membrane which has been impregnated with a dry chemistry reagent system specific for analysis of an analyte within the heterogeneous fluid sample, said membrane having a sample receptive surface of sufficient density to selectively exclude substantial penetration of suspended or dissolved matter of the sample which can interfere or mask the reaction of the analyte with the reagent system in the membrane, while allowing the remainder of the sample to be freely absorbed; and a fluid impermeable barrier layer located between the wicking element and the sample receptive surface of said porous membrane for maintaining said wicking element out of fluid contact with said receptive surface, said barrier layer having at least one aperture for confinement of a pool of sample on the sample receptive surface of the porous membrane, the size and shape of said aperture permitting flow of the heterogeneous fluid sample from the wicking element to the sample receptive surface of the membrane and roughly corresponding to an analysis site.

2. The self-contained analytical element of claim 1, wherein the surface of the wicking element which is contiguous with the barrier layer is modified to facilitate the flow of sample from the wicking element to the sample receptive surface of the porous membrane, said modification involving the placement of a series of channels or cuts in the surface of said wicking element in the area corresponding to the aperture of the barrier layer.

3. The self-contained analytical element of claim 1, wherein the heterogenous fluid sample is whole blood and the wicking element is transportive of the whole blood sample to the sample receptive surface of the porous membrane.

4. The self-contained analytical element of claim 3, wherein the dry chemistry reagent system is specific for the manifestation of glucose in whole blood.

5. In a disposable fixture adapted for use in a portable self-test monitor designed for detection of constituents of whole blood, the disposable test fixture being provided with a test strip and means for inflicting a puncture wound sufficient to draw blood, the improvement comprising:

a test strip consisting essentially of two functional components, each of said functional components being maintained in spaced apart relationship and out of fluid contact with one another by a fluid impermeable barrier layer:

(a) a first functional component of said test strip comprising an essentially planar wicking element for reception of the whole blood sample and transport of the whole blood sample to a dry chemistry reagent system;

(b) a second functional component comprising an essentially planar porous membrane which has been impregnated with a dry chemistry reagent system specific for analysis of a constituent within the blood sample, said membrane having a sample receptive surface of sufficient density to selectively exclude substantial penetration of cellular components of the blood into the membrane while allowing fluid components to be freely absorbed; and (c) a fluid impermeable barrier layer comprising an essentially planar element, located between the wicking element and the sample receptive surface of said porous membrane, for maintaining said wicking element out of fluid contact with said receptive surface, said barrier layer having at least one aperture, for confinement of a pool of blood on the sample receptive surface of the porous membrane, the size and shape of said aperture permitting flow of the whole blood from the wicking element to the sample receptive surface of the membrane and roughly corresponding to an analysis site which is defined in terms of the field of view of a photo-optical read station of said monitor.

6. The improvement of claim 5, wherein the dry chemistry reagent system is specific for the manifestation of glucose in the whole blood sample.

7. The improvement of claim 5, wherein the surface of the wicking element which is contiguous with the barrier layer is modified to facilitate the flow of the whole blood sample from the wicking element to the sample receptor surface of the porous membrane, and modification involving the placement of a series of channels or cuts in the surface of said wicking element in the area corresponding to the aperture of the barrier layer.

* * * * *